US006577134B2

(12) United States Patent
Farruggia et al.

(10) Patent No.: US 6,577,134 B2
(45) Date of Patent: Jun. 10, 2003

(54) SENSOR AND SENSOR SYSTEM FOR LIQUID CONDUCTIVITY, TEMPERATURE AND DEPTH

(75) Inventors: Guy J. Farruggia, Ellicott City, MD (US); Allan B. Fraser, Woodbine, MD (US)

(73) Assignee: Areté Associates, Sherman Oaks, CA (US)

( * ) Notice: Subject to any disclaimer, the term of this patent is extended or adjusted under 35 U.S.C. 154(b) by 0 days.

(21) Appl. No.: 10/010,936

(22) Filed: Dec. 6, 2001

(65) Prior Publication Data

US 2002/0135377 A1 Sep. 26, 2002

Related U.S. Application Data

(62) Division of application No. 09/562,849, filed on May 1, 2000, now Pat. No. 6,404,204.

(51) Int. Cl.[7] .......................... G01N 27/42; G01N 27/02
(52) U.S. Cl. ..................... 324/425; 324/441; 324/439; 324/448; 324/444; 324/158.1
(58) Field of Search ................. 324/425, 439, 324/441, 448, 444, 158.1, 442, 693; 29/832

(56) References Cited

U.S. PATENT DOCUMENTS

| | | | | |
|---|---|---|---|---|
| 3,835,371 A | * | 9/1974 | Mirdadian et al. ............. 324/3 |
| 3,906,353 A | * | 9/1975 | Murdock ..................... 324/442 |
| 3,991,623 A | * | 11/1976 | Murdock ..................... 73/170 A |
| 4,193,291 A | * | 3/1980 | Lynnworth ................... 73/32 A |
| 4,208,906 A | * | 6/1980 | Roberts, Jr. ................... 73/155 |
| 4,225,410 A | * | 9/1980 | Pace ........................... 204/412 |
| 4,558,714 A | * | 12/1985 | Frigiola .......................... 137/2 |
| 4,655,880 A | * | 4/1987 | Liu ........................... 205/777.5 |
| 4,676,252 A | * | 6/1987 | Trautman et al. ........... 600/484 |
| 4,876,904 A | * | 10/1989 | Limon .......................... 73/866 |
| 4,900,921 A | * | 2/1990 | Spillman, Jr. ................ 250/227 |
| 5,255,427 A | * | 10/1993 | Hafner ........................ 29/621.1 |
| 5,336,388 A | * | 8/1994 | Leader et al. ................ 204/403 |
| 5,342,498 A | * | 8/1994 | Graves et al. .............. 204/408 |
| 5,342,510 A | * | 8/1994 | Eden et al. ................. 210/96.1 |
| 5,355,312 A | * | 10/1994 | Tostoy et al. .................. 702/18 |
| 5,367,911 A | * | 11/1994 | Jewell et al. ............. 73/861.08 |
| 5,483,164 A | * | 1/1996 | Moss et al. .................. 324/425 |
| 5,546,004 A | * | 8/1996 | Schmelz ...................... 324/446 |
| 5,757,197 A | * | 5/1998 | O'Neill ....................... 324/696 |
| 5,790,476 A | * | 8/1998 | Stenstrom et al. .......... 367/120 |
| 5,895,595 A | * | 4/1999 | Steininger et al. ............ 210/85 |
| 5,944,495 A | * | 8/1999 | Jacobbsen et al. .......... 417/415 |
| 6,098,457 A | * | 8/2000 | Poole ........................... 73/295 |
| 6,119,508 A | * | 9/2000 | Tarui et al. ................. 73/53.01 |
| 6,201,980 B1 | * | 3/2001 | Darrow et al. .............. 600/347 |
| 6,226,994 B1 | * | 5/2001 | Yamada et al. ................ 62/37 |
| 6,277,078 B1 | * | 8/2001 | Porat et al. .................. 600/486 |

* cited by examiner

Primary Examiner—N. Le
Assistant Examiner—Wasseem H. Hamdan
(74) Attorney, Agent, or Firm—Peter I. Lippman

(57) ABSTRACT

Liquid conductivity and temperature are measured in respective sensitivity fields that are collocated—i. e., in volumes that nearly match by mathematical, geometrical, or functional criteria. Collocation is as distinct from mere adjacency or proximity; and is with respect to measurement volumes, not measuring hardware. Preferably pressure too is measured with sensitivity very generally collocated to the conductivity and temperature sensitivity. Preferably, respective temporal/spatial bandwidths of the two (or three) sensors are matched. Preferably the pressure sensor is a MEMS transducer, the conductivity sensor is a four-terminal device, the thermometer is a thermistor encapsulated in a silkscreened glass wall, and circuits (1) compensate for time lag between conductivity and temperature measurement, (2) remove artifacts due to detritus in or near either sensor, and (3) derive secondary parameters of the liquid.

46 Claims, 8 Drawing Sheets

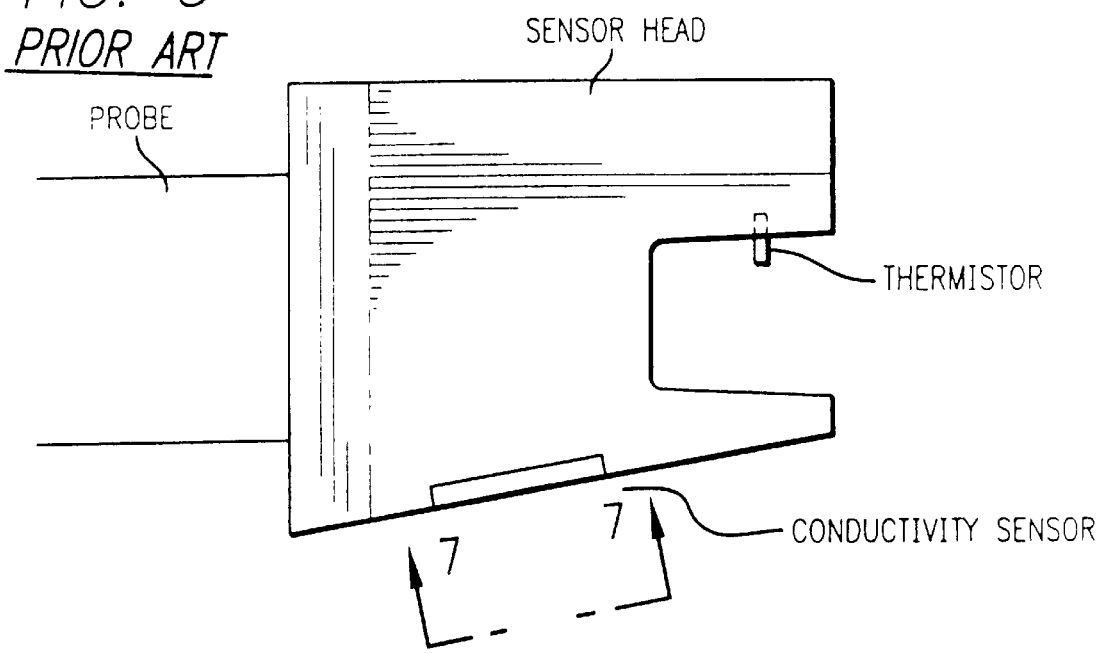
FIG. 5 PRIOR ART
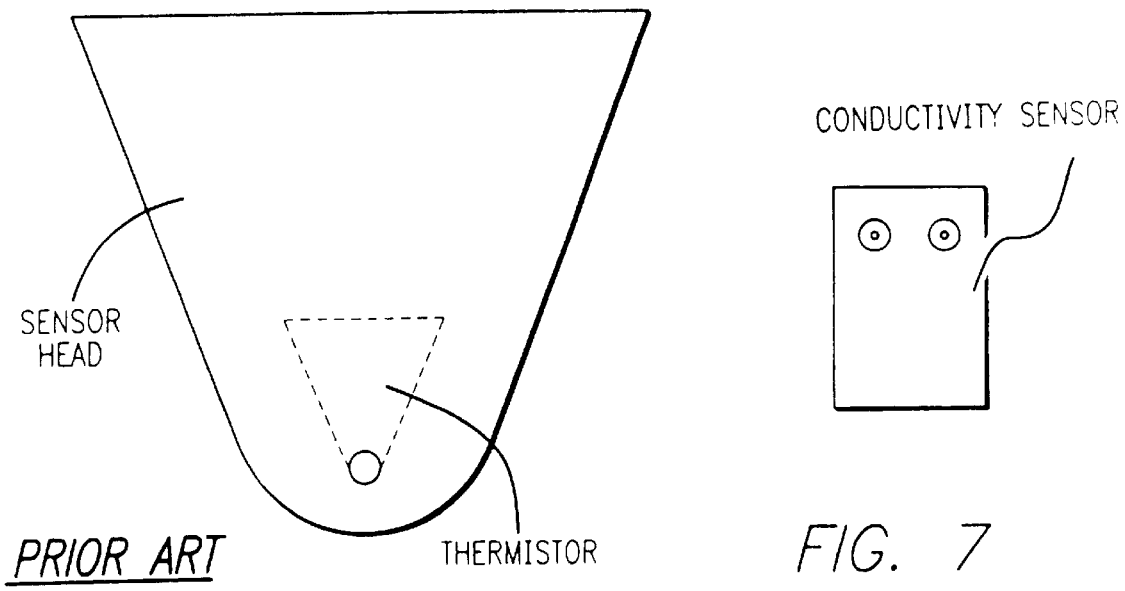
FIG. 6 PRIOR ART
FIG. 7 PRIOR ART

FIG. 7A
PRIOR ART
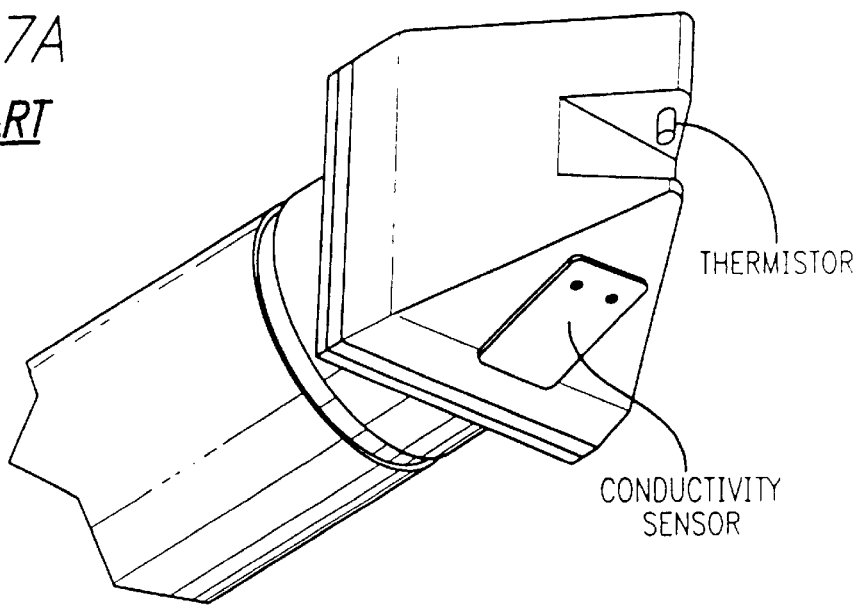
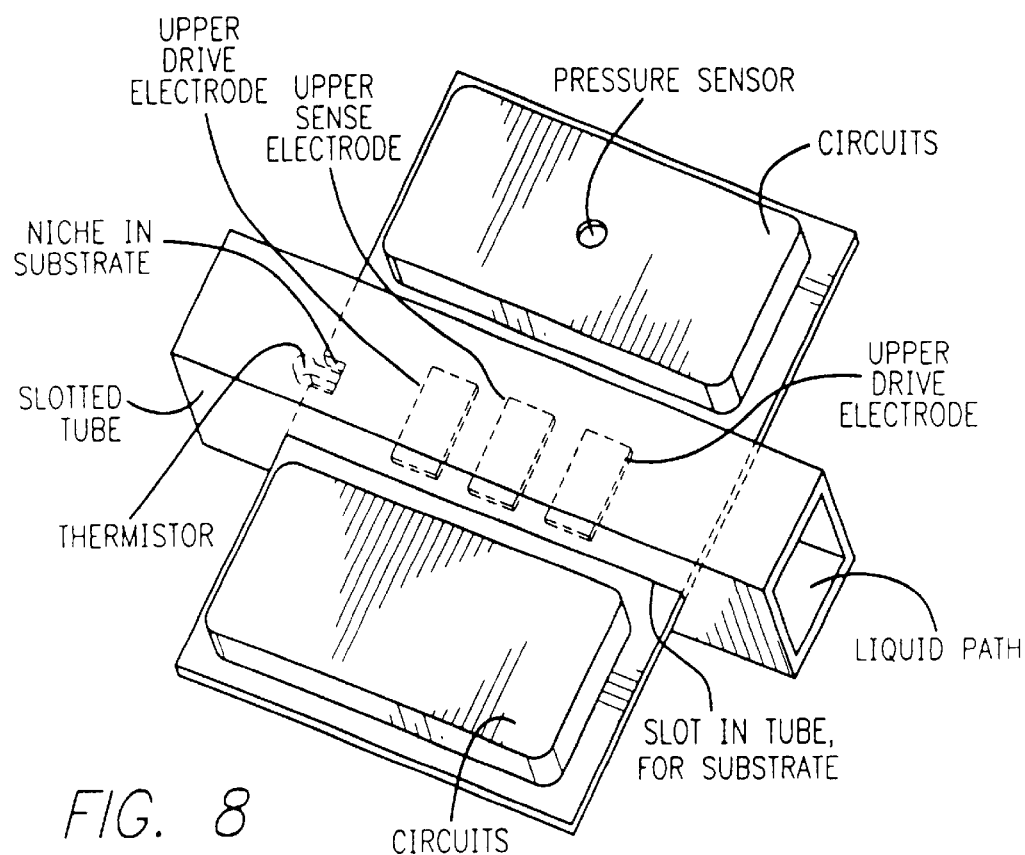
FIG. 8

SENSOR AND SENSOR SYSTEM FOR LIQUID CONDUCTIVITY, TEMPERATURE AND DEPTH

This is a divisional of application Ser. No. 09/562,849 filed on May 1, 2000, now U.S. Pat. No. 6,404,204 B1, patented on Jun. 11, 2002.

BACKGROUND

1. Field of the Invention

This invention relates generally to apparatus for monitoring and measuring electrical and thermal properties of liquids including saline water and other conductive solutions; and more particularly to a device that can be used to measure such properties, preliminary to very accurately deriving therefrom secondary properties—such as salinity, density and the speed of sound in such liquids. Preferably the apparatus also measures water pressure, preliminary to determining depth.

2. Related Art

Temperature and electrical conductivity are among the most fundamental parameters that characterize liquids in three spatial dimensions and time. Measurement of these quantities enables derivation of various parameters including salinity, density and sound speed. These derived parameters are fundamental for many different kinds of determinations.

These range, for example, from studying stability and mixing processes in the ocean—for fundamental physical oceanographic knowledge, and for understanding the environmental and biological processes in the sea—to acoustic techniques for locating objects, or determining the direction and velocity of objects, in water. Still other determinations include sensing of disturbances in density-stratified water.

All such techniques are outside the scope of this document being well known and straightforward to apply—given usable values of salinity, density, sound speed and depth.

This latter parameter, depth, historically has been evaluated from probe drop rate. (This is true particularly of previous devices intended to be used just once and discarded, i. e. not retrieved.) Various uncontrolled factors make this approach objectionably imprecise.

In this document, devices for sensing conductivity, temperature and depth by concurrent measurements are called "CTD" sensors or simply "CTDs". Those intended for one-time use, i. e. units that are nominally expendable, are called "XCTDs".

Technology is available for measuring temperature and conductivity in the context of oceanographic research. Accuracy of measurements, however, in the use of such available technology, is for many purposes less than satisfactory.

There have been significant limitations in the accuracy of derived parameters such as sound speed, salinity and density. More specifically, it is accuracy in the derived parameters—primarily density, and speed of sound—which leaves much to be desired.

The present inventors have studied this problem and have gained understandings of the sources of such inaccuracy. Some of these insights are probably known to advanced artisans in related work, particularly perhaps to some scientists in oceanography.

Thus for instance it may be recognized that significant error components arise from failure to collocate the temperature and conductivity sensors. In other words, for good accuracy the sensors should be arranged so that the liquid volumes whose temperature and conductivity, respectively, are measured are a common volume—to a reasonable degree of precision.

Other related understandings, however, are believed to be novel at least in part, as seen from the perspective of a person of ordinary skill in the art of monitoring instrumentation. These insights therefore will be presented in later sections of this document which disclose the invention.

Temperature measurement—Previous work of the present inventors has provided thermistor-based temperature measurements with longterm accuracies better than 15 mdeg. The temporal resolution of the temperature in the ocean was better than 7 msec, and the temperature resolution in the microdegree range.

A simple but stable half bridge was used for the temperature sensor circuit. As will be seen, such devices are advantageously adapted for use in a novel combination CTD device.

Conductivity measurement, and combined conductivity/temperature sensors—Another limitation of measurement apparatus heretofore known is that the apparatus is in fact clearly addressed to research applications. Reasonably economical higher-volume units for robust, routine use in—for example—waterway or ocean monitoring have yet to be introduced.

The prior art of CTD sensors may be divided into two categories: expendable and nonexpendable devices. At this writing there is only one source of expendable CTDs, or XCTDs, on the market. There are several sources of non-expendable CTDs.

Nearly all of these devices use thermistor-based temperature sensors. Thermistors are very stable and easily encapsulated—and they come in a variety of shapes, resistance ranges, and response times.

Available CTDs use various positions of the thermistor near the conductivity cell. To date there are no nonexpendable CTDs that have the thermistor placed directly into the sampling volume of the conductivity cell.

The one expendable commercial probe encloses both the conductivity cell and thermistor in a tube 20 cm (eight inches) long, thus approaching collocation but not achieving it. That device, and many of the nonexpendable CTDs as well, use electrode-type conductivity sensors.

Most of these cells, but not that of Sea-Bird Corporation, use a four-electrode design. Sea-Bird uses a three-electrode cell that is within a Wien bridge.

All of these conductivity cells are of a closed geometry. Such geometry maximizes d. c. stability at the expense of frequency response.

An inherent problem with most closed-geometry cells is that the approach does not easily lend itself to mass production. Placing or forming electrodes on the inside of a tube, by common methods, is costly and time-consuming. Handcrafting of the conductivity cell is a major cost driver of an expendable device.

Other prior conductivity cells use open-celled geometries, which the present inventors have described earlier but never commercialized. These cells were designed for doing high-frequency measurements, and not maximized for d. c. or low-frequency stability.

When expendable sensors are used in ocean-water monitoring, the cost of the discarded sensors is very high. When nonexpendable sensors are used in ocean monitoring, the sensor cost is allocated over a much greater number of studies—but an important secondary problem arises in the high cost of equipment, and also of crew and staff time, required simply for reeling the sensors back up to the surface after each probe drop.

Even taking into account the economy available through multiple reuses, today's available sensor technology is expensive when used in an expendable form. An expendable conductivity, temperature, and depth sensor ("XCTD") costs an order of magnitude more than expendable temperature probes (XBTs) alone.

The present invention contemplates reducing the cost of XCTDs, including a depth measurement, to a level that is half the cost of a now standard XCTD, or less—perhaps approaching an order of magnitude less. One such standard unit, essentially handmade, costs $500 each in dozen lots; but expendable bathythermographs (XBTs) can cost as little as $50 per sensor. This order-of-magnitude cost difference between XBTs and XCTDs represents a major barrier to widespread use of the more desirable XCTDs.

Over the past two decades, significant progress has been made in the measurement of temperature and conductivity in the ocean. Preferred embodiments of the present invention are improvements over technology developed by the present inventors originally for high-frequency conductivity turbulence measurements.

The development of that earlier technology sensor started in the early 1980s when the present inventors were at The Johns Hopkins University Applied Physics Laboratory and introduced a four-electrode sensor—described in Farruggia, G. J., Fraser, A. B., "A Miniature Towed Conductivity Apparatus," *Proceedings Of Oceans,* Sep. 10–12, 1984. That basic configuration underwent ongoing refinement during ensuing years, though none of those changes included the present invention.

That reusable sensor was developed to be small, robust, nonfouling, high-bandwidth conductivity measurement device, and inexpensive—though associated electronics and special housing were quite costly. Its main purpose was to measure turbulent patches in the ocean.

The open-face planar design of the cell was not optimized for longterm absolute accuracy. In the early—to mid 1990s, the cell geometry was modified to enhance longterm stability.

Two test series used sensors with opposed electrode patterns within a generally open flow channel (FIGS. 1 and 4)—but not quite as open and resistant to fouling as the open-face planar units mentioned just above. These sensors were transported underwater horizontally and vertically on towed arrays and dipping systems—and were very successful.

Calibrations were stable over a five-month measurement period and were favorably comparable to specifications of available CTDs. Opposed sensors of this general type are adaptable for use with certain specific aspects of the present invention.

These several conductivity cells were fabricated using a platinum-alloy thick film deposited on a ceramic substrate. Deposition of an alloy of platinum, a noble metal, was chosen so that only the most electrochemically stable surface would be exposed to seawater.

In later years a new generation of open, planar cells was developed using low-temperature cofired ceramic (LTCC). This method enabled the multiple layers of the circuit substrate to be put down and stacked, then pressed, and finally fired to make the multilayer board in one unitary sequence of steps.

Multiple sensors were fired on a common board and then cut into shape for use. LTCC was a significant improvement because the sensors were more easily fabricated and their assembly simplified—and as planar, open designs they were good for high-frequency response and also highly resistant to fouling.

The electrodes of these cells were also platinized—a finely divided coating of black platinum metal was electroplated on the electrodes to reduce the surface contact impedance of the electrode/seawater interface. In the more-advanced versions, the LTCC approach conferred good encapsulation of metallizing under layers of glass, thereby tending to protect the electrodes well.

Nevertheless these units shared with other planar designs an undesirable susceptibility to erosion of the electrodes. They also suffered from poor low-frequency response, which is particularly troublesome in certain applications that demand direct-current (or very slowly varying) operation.

Electronics provided for the best of these ocean electrical conductivity sensors comprised a classical four-electrode system—two electrodes to force current through a sample, and two others to sense resultant voltage. The circuits operated on high-frequency alternating-current to minimize electrode corrosion and impedance.

Voltage difference between the sensing electrodes was held to a specific value by a servo circuit that adjusted the magnitude of the driven current. To keep stray current out of the measurement path, sensor operating power was carefully isolated from circuit returns involving the host system.

The best of these units, like the thermistor advances mentioned briefly earlier, are adaptable for use in an improved combination device. In doing so, however, some provision is needed to avoid errors due to particulates confounding the measurements made with the cell.

Conductivity measurements, particularly but not only at high spatial frequencies, are further confused by small particles which pass through a sampling cell. These particles, usually either plankton or detritus, are common in the sea. When such particles pass through the conductivity sensor they exclude, or replace, some of the volume of water that would otherwise occupy the sensor; thus the conductivity measured is not only that of the water itself.

These variations can cause noticeable errors in the conductivity measurements, and significant errors in the derived quantities. Fraser, while at Johns Hopkins, developed nonlinear circuitry to remove most of these fluctuations due to particle passage through the cell.

This circuitry recognized the rapid rise of brief conductivity changes and substituted the immediately preceding signal value for the transient. As will be seen, the benefits of this work can be adapted in combination with aspects of the present invention to provide a more highly advanced and more accurate measuring package, in more robust form and at lower cost.

At this writing there is only one commercial source of an XCTD. It is a very good sensor, but has a main drawback that each unit is essentially handmade—which increases production costs, leading to a relatively high cost for each sensor.

In addition as noted earlier these units are sold only in lots—further increasing the investment—and require a specialized data acquisition system, or investment in a frequency-decoding system. The cost and lot-sale basis alone imply a minimum $6,000 investment in sensors—even without considering the cost of the companion data system.

Published performance specifications for the XCTD under discussion here—which is a product of the Sippican Corporation are listed below. These specifications are modest, and it is desirable to meet or considerably exceed them.

| Temperature: | Range | −2.2 to +30 ° C. |
|---|---|---|
|  | Accuracy | ±0.035 ° C. |
| Conductivity | Range | 20 to 75 mS/cm |
|  | Accuracy | ±0.035 mS/cm |
| Depth | Range | 0 to 1000 m |
|  | Accuracy | ±5 m or 2% of depth |
| Vertical Resolution |  | 1 m |

The depth value given in the above specifications is a derived quantity based on a standard probe drop rate. Generally speaking this commercial product performs well and serves a valuable purpose; and it is not the intention here to derogate it.

Nevertheless as mentioned earlier, values of sound speed and density derived from measurements with this unit are subject to objectionable inaccuracies, and it is very costly. In addition, for some types of routine operation this device is not sufficiently robust.

As can now be seen, the related art remains subject to significant problems, and the efforts outlined above—although praiseworthy—have left room for considerable refinement.

SUMMARY OF THE DISCLOSURE

The present invention introduces such refinement, and overcomes the several above-discussed prior-art limitations. These include derived-quantity accuracy, robustness for routine operational uses, and cost.

Informal orientation—The invention has several independent aspects or facets, which can be practiced independently but for best results are advantageously used in combination together. Before giving a definitive presentation of the invention itself, however, this document will offer—only in the nature of a preliminary orientation—some insights which are believed to represent a part of the inventive process.

As previously indicated, these observations go to the identification of error sources to which prior devices are susceptible. It will be recalled that the inaccuracies under consideration arise especially in the values of the derived parameters—particularly salinity, density and speed of sound. As to depth determination the invention also offers a major improvement in accuracy as compared with the drop-rate method.

In particular the present inventors have noted that relatively large errors in the first three derived parameters seem to result from taking measurements of the primary parameters (conductivity, temperature and pressure) that are not properly combinable. The conductivity and temperature measurements are not only at slightly different locations but also are measured through different temporal and spatial bandwidths—and furthermore are subject to temporal offsets.

In other words, the two main measuring instruments do not measure exactly the same water mass in a combinable fashion leading to good accuracy. Not only are they in poor mechanical registration or collocation, but also have different frequency response and different wavenumber (spatial periodicity) response (FIG. 1A).

Although it is likely or possible that advanced researchers have appreciated the collocation problem, this problem has not been corrected in known devices. In addition it appears that the instrumentation art has failed to recognize—and certainly failed to address—the bandwidth and time-offset problems.

These observations appear to explain failure to realize expectable precision and accuracy, heretofore, under unknown conditions of water flow and thermal gradient. In effect the water volume whose conductivity is being measured is a different volume from that whose temperature is being measured.

When measurements taken with two sensors are then combined to find the derived parameters, the results are inherently flawed—because the derivations are strictly valid only for measurement in an identical volume. The mismatches of location are readily large enough to account for at least the greater part of observed error. Also, analogous mismatches in the presence of a very steep pressure gradient may disturb derived-parameter accuracy in some industrial applications, though probably not in the sea.

Thus these insights favor construction of the sensors in a tightly integrated package that makes the effective location of the measurement volume of water identical for all three measurements. This document will refer to this mutual-location requirement as the "collocation" requirement.

Even more subtlety favored is construction that better matches the spatial and temporal bandwidths for the conductivity and temperature measurements—and pressure as well, for those special measuring environments in which pressure varies strongly enough to produce a like problem. In some situations even though bandwidths are matched one of the measurements may suffer an effective lead or lag.

In view of these remarks it will now be clear, to a person of ordinary skill in the art, that patterns of water flow—and of gradients in temperature, conductivity and even pressure—should be given some consideration in configuring sensors. As will be seen, where an actual match of bandwidth or synchronization is not feasible or is uneconomic, data can be compensated to correct for mismatch.

In short, bandwidth-matching and spatial and temporal collocation of the sensors are a problem for existing sensors, limiting the accuracy of the quantities to be derived. The solution is an integrated sensor that measures, simultaneously and at the same location—and in the same temporal and spatial bandwidths as well—both temperature and electrical conductivity.

The same is true for pressure, in industrial or other environments presenting significant pressure gradients. The solution also encompasses data compensation, where this is more practical or cost-effective than actual bandwidth and temporal matching.

From these measurements one can derive the three previously identified secondary parameters with very greatly enhanced accuracy. The accuracy improvement comes directly from the collocation, bandwidth matching and synchronization.

In addition to accuracy, the invention is improved as to sturdiness, reliability and cost. Much larger electrodes—providing a high ratio of electrode surface to edge, make the device resistant to a degree of erosion.

Furthermore a longer conduction path, in relation to electrode dimensions, makes the path a larger fraction of the resistance in the circuit—still further reducing the measurement-disrupting effects of whatever erosion does occur. By moving away from handcrafted devices to items that can be mass-produced, the invention reduces cost very substantially.

From what follows it will be clear that the configuration of the present invention needs no demonstration to establish great hardiness in field operation. Similarly it will be immediately clear that the invention is amenable to mass-producibility and remarkably improved production and sale economics.

A first primary aspect of the invention—Now with the foregoing informal orientation in mind, this document proceeds to a somewhat more rigorous discussion or definition of the invention itself. The invention has several independently usable facets or aspects, all but one of which are—in their preferred embodiments—apparatus for determining parameters of a liquid.

The several independent facets or aspects, although independently usable, are nevertheless very advantageously used in combination, to achieve the best and highest benefits of the invention. This is so because the various facets of the invention interact with one another in important beneficial ways, as will be seen.

In preferred embodiments of its first independent aspect or facet, the apparatus of the invention includes a conductivity sensor for measuring electrical conductivity of such a liquid. It also includes a thermometer for measuring temperature of such a liquid.

A sensitivity field of the conductivity sensor and a sensitivity field of the thermometer are substantially collocated, i. e. effectively located together. People of ordinary skill in the field of combined conductivity and temperature instrumentation will have a good instinctive understanding of collocation.

Such instinctual understanding for most such skilled people will perhaps be in terms of both resulting measurements somehow relating to a common volume of water. If this condition is met, is reasonable to combine the measurements in calculations of derived parameters.

Working definition of collocation—This concept of collocation, however, is somewhat surprisingly difficult or awkward to define in a quantitative or rigorous way. The reason for this difficulty is in large part that liquid-conductivity and -temperature sensors do not ordinarily detect conductivity (or even temperature) within a simple, well-defined volume of liquid.

Instead each sensor has a response profile or sensitivity function that is distributed in space (and usually also in time) in complicated ways. The response is usually strong and concentrated in a region near the sensitive element or elements. As those in this field will recognize immediately, the response is particularly strong between sensitive elements of opposite polarity, in the case of electrical conductivity probes—but is weak, tenuous and dissipated in more-remote regions of the sensed space.

Response shapes, too, may vary in particular as between conductivity and temperature sensors. The response of a thermistor, for instance, is generally a comet-shaped function, trailing behind the sensor if it moves through the liquid, and affected by liquid which includes some volume elements at a considerable distance from the physical sensor.

In many cases the sensing profile of conductivity and temperature sensors alike extends, in purest principle, to infinity. Of course if the sensing profile of a first sensor extends to infinity then a second sensor is necessarily disposed entirely within the sensing profile of the first.

Thus if "collocation" were defined as merely having one sensor within the sensing field of the other, then the foregoing discussion would lead to the conclusion that all sensor pairs are collocated. The same illogical result arises from attempting to merely define collocation as inclusion or nesting of one sensor's sensitive profile within the other.

On the other hand, some instinctively reasonable definitions of collocation lead to unreasonably restrictive results. Thus for instance physical positioning of one sensor wholly within the other produces good results, usually, and therefore may be regarded as good collocation, but this is an extreme case, not at all a requirement for good collocation.

Even so, it is possible to position one sensor entirely within the other (or the sensitive field of one sensor entirely within the sensitive field of the other) and still obtain rather poor measuring-signal combinability. Hence the nesting concept is at once neither a requirement nor a guarantee of effective collocation—i. e., it is neither necessary nor sufficient.

Exactly perfect coextensiveness of liquid volumes sensed by the two sensor fields may be considered a paradigm of collocation—but again, this geometry too is unnecessarily restrictive and yet may not be sufficient. It is also extremely difficult, if not impossible, to achieve.

Another interesting case focuses upon the source of the liquid, and whether it has been well mixed—within the scale of the fine structure of gradients and flows in the liquid—before arriving at the two sensors. If it has been thus well mixed, then the sensors may be relatively far apart and nevertheless produce paramountly combinable signals.

Yet another illuminating case involves a sensor whose sensitivity profile has plural lobes, i. e. plural concentrations of sensitivity distribution. In such a geometry it is often an excellent solution to place the other sensor (or its sensitivity profile) between those plural lobes; yet at that precise point often the first sensor has virtually no sensitivity at all.

Some effort has been given to defining collocation in terms of a more sophisticated mathematical formulation. In particular the strengths of the two sensitivity fields at each point throughout space can be multiplied together, and the resulting product added up throughout the space—i. e., integrated using integral calculus.

Such a calculation is said to form a "crosscorrelation coefficient". The two sensitivity profiles are usually extremely irregular and not readily amenable to crosscorrelation calculation by closed algebraic methods. Nevertheless, in general the two profiles can be carefully measured separately, given the anticipated surrounding apparatus, and then the crosscorrelation formed using well-known and entirely standard numerical methods in a computer.

It is not necessary that a person interested in this art and wishing to evaluate the scope this invention be able to work integral-calculus problems as such—since many mathematics computer programs such as MathLab® are now available which perform such functions automatically. Many persons of ordinary skill in this field, such as journeyman programmers, are very comfortable with use of these now-familiar tools.

For those who may be academically or otherwise interested, however, the essential idea of the crosscorrelation is to integrate the product of two sensitivity functions $F_1$, $F_2$ over the entire measurement space. For open sensor geometries this is in principle all of space, but as a practical matter can be limited to regions in which either or both $F_1$, $F_2$ are at least some specified fraction of their maximum central values.

That fraction may for example be set at one thousandth or one hundred-thousandth, or for special cases at a considerably larger value such as one tenth or even more. It will be clear with a very minimum of trial and error where the threshold can be set to give meaningful results without unnecessarily protracted computation.

The two sensitivity profile strengths are simply multiplied together, $F_1 \cdot F_2$, for each particular small volume of the measurement space. For simplest processing all the small volumes (differential volumes) should be the same size. Then all the products can be simply added together, and that sum is the integral—which may be designated $C_{ACTUAL}$ for the crosscorrelation coefficient of any actual geometry and assumed sensor sensitivity patterns used in the calculation.

This provides a good measure of collocation, provided that certain constraints are observed. In forming and using this measure it would be very difficult to take account of the characteristics of the liquid, or of any possible premixing of the liquid, or of time effects as between the two sensors.

As to "time effects" it must be realized that the maximum (or cumulative maximum) or responses from the two sensors do not necessarily occur in synchronism. An ideal collocation measure should not be susceptible to corruption of results by any of these liquid-characteristic, or premix, or time-related, confusing factors.

An opposite and even more ideal approach would be to form a collocation measure that is a much higher-order field, fully taking into account the body of liquid involved—e. g., the sea, with all its complex statistical properties and allowing for the distance and time scales of interest. Such a measure would expectably be tiny for known sensor packages—and an excellent new package might be into the range above 0.99; however, actually constructing such a measure of collocation would in itself be a major endeavor.

The objective here, after all, is merely to be able to characterize, quantify or compare the practical scope of the present invention with competing devices (or relevant priorart devices). The objective of defining collocation is not to solve a fundamental oceanographic puzzle.

If a crosscorrelation coefficient is calculated on a purely geometrical basis, without regard to any of these three factors, then it does provide an excellent measure of collocation for many cases. Moreover it is advantageous in that it encompasses the effects of attempts to dilate or contract the sensing profile of one or the other sensor.

On the other hand, by virtue of this particular advantage this form of crosscorrelation approach is somewhat disadvantageous in that it produces very low numbers for most practical configurations. It is probably well under 0.1 for all geometries that have ever been either reported in the literature or commercialized. Although an ideal value may be identified as unity, such an achievement would appear unattainable for at least many or most cases of greatest practical interest.

Therefore it is not readily evaluated instinctively by persons having ordinary skill in this particular instrumentation art. One reason for these low numerical results is that the most intensely sensitive measuring regions of the two sensors are usually very different in size or shape, and usually both.

An alternative approach, therefore, is a form of normalization: this approach instead forms a ratio of two crosscorrelation coefficients. One is the coefficient $C_{ACTUAL}$ described above, calculated for a particular relative electrode placement of interest—that is, a candidate positioning of the two different sensors with respect to each other.

The second coefficient $C_{IDEAL}$ is again the same calculation, but now instead calculated using the ideal best relative positioning that can be found, for those two practical, real world sensors. In this case it is tacitly assumed that such a relative positioning exists and can be evaluated.

When this is done, the ideal output value for the ratio $C_{ACTUAL}/C_{IDAL}$ is still unity, but now the scale of goodness for many or most cases extends definitely to and including that value—because the denominator of the ratio is almost by definition attainable. This measure $C_{ACTUAL}/C_{IDEAL}$ of collocation is therefore much more readily evaluated on an instinctive basis by persons of ordinary skill.

This measure cannot, however, provide any comparison that takes into account the possibility of adjusting the absolute sizes or shapes of the spatial profiles toward one another. Of course, this is appropriate because the very purpose of forming this normalized measure is to avoid the influence of such effects.

Furthermore, as already mentioned both of the crosscorrelation approaches are still incapable of taking into account liquid mixing, time effects, or many special geometries.

Accordingly it appears that no single measure of collocation can be adequate to identify highly favorable geometries. For purposes of this document, therefore, and particularly for purposes of the appended claims, "substantial collocation" is defined as satisfaction of at least one of these criteria:

a crosscorrelation coefficient $C_{ACTUAL}$ for the two fields, calculated geometrically without regard to characteristics of such liquid, and assuming no mixing of such liquid and is no spatial lag, is between 0.01 and unity, a ratio $C_{ACTUAL}/C_{IDEAL}$ of (a) crosscorrelation coefficient for the two fields in their actual relative locations to (b) crosscorrelation coefficient for said two fields in ideal relative locations but without change of relative size, both coefficients being calculated geometrically without regard to characteristics of such liquid, and assuming no mixing of such liquid and no spatial lag, is between 0.9 and unity, one sensor is positioned between plural primary lobes of the other's sensitivity function, one of the sensors is positioned within a most direct path of sensitivity field lines of the other sensor, the two fields effectively monitor substantially identical volumes of such liquid, the two fields effectively monitor volumes of such liquid that are nested, and the two sensors both monitor volumes of such liquid sampled from a common mixing volume.

In the articulation of these criteria, the phrases "primary lobes" and "most direct path of sensitivity field lines" are used in their literal meanings but will become even more clear from what follows in this document. The word "effectively" is defined to mean specifically that the monitoring is to take into account only volumes that are very sensitively probed—in other words, only volumes where sensitivity is strong or concentrated.

In other words, as a practical matter regions where sensitivity is weak, such as less than ten percent of the maximum value, are simply disregarded. The threshold for this purpose may vary from five to twenty-five percent depending on the geometry, as those of ordinary skill in the art will clearly understand.

In essence this is another way to characterize the interactive effects of two sensitivity fields, but to do so without calculating crosscorrelations. On the other hand, one rather advanced mathematical approach to conceptualizing these particular criteria is to say that the impulse responses are collocated within a selected small threshold value.

The foregoing may represent a description or definition of the first aspect or facet of the invention in its broadest or most general form. Even as couched in these broad terms, however, it can be seen that this facet of the invention importantly advances the art.

In particular, an apparatus as above defined, which satisfies any one or more of the listed criteria, produces measurements from the two sensors that can be combined in calculations to yield very accurate derived parameters. It is believed that prior devices have never satisfied any of these criteria.

Although the first major aspect of the invention thus significantly advances the art, nevertheless to optimize enjoyment of its benefits preferably the invention is practiced in conjunction with certain additional features or characteristics. In particular, preferably the device also includes a pressure sensor for measuring pressure in a pressure-measurement volume of such liquid; and a sensitivity field of the pressure sensor is very generally collocated with the conductivity- and temperature-measurement sensitivity fields.

The terminology "very generally collocated" is intended to be much more inclusive than "substantially collocated", since the requirement on pressure collocation for good measurement combinability is correspondingly much less stringent. There are two reasons: first, pressure gradients in many or most practical applications are much less steep than those of temperature and conductivity.

Second, in fact the pressure (or resulting depth value) is most often used as an independent variable. In other words the conductivity, temperature, and parameters derived from those values are usually plotted against pressure—so that the "combination" of the raw data in calculations is of a wholly different order and character, much less demanding.

Another preference is that the pressure sensor, if present, be mounted in a common unitary assembly with the conductivity and temperature sensors. Preferably the pressure sensor is a MEMS transducer, the conductivity sensor a four-terminal device, and the thermometer a thermistor encapsulated within a silkscreened glass wall.

Also preferably included is a data-acquisition and data-processing system fabricated in a substantially unitary assembly with the sensors, and connected to receive measurement signals from the sensors. This system includes circuits for deriving from the measurement signals secondary parameters of such liquid for said substantially identical measurement volumes. Preferably the secondary parameters include density and speed of sound—and, with a pressure sensor included, depth as well.

A second primary aspect of the invention—In preferred embodiments of its second major independent facet or aspect, the invention apparatus includes a conductivity sensor for measuring electrical conductivity of such liquid. This sensor has a temporal response bandwidth and a spatial response bandwidth.

Also included is a thermometer for measuring temperature of such liquid. The thermometer has a temporal response bandwidth and a spatial response bandwidth.

The temporal response bandwidths of the conductivity sensor and thermometer are effectively matched. Also the spatial response bandwidths of the conductivity sensor and thermometer are effectively matched.

The foregoing may represent a description or definition of the second aspect or facet of the invention in its broadest or most general form. Even as couched in these broad terms, however, it can be seen that this facet of the invention importantly advances the art.

In particular, bandwidth matching provides an additional increment of accuracy in the derived parameters, separate from that obtained through collocation. Some of the derived parameters are highly sensitive to small fluctuations of the primary measured parameters.

In the ocean, for example, small residual errors have an extremely disproportionate effect on derived values of density. The power spectrum of temperature, conductivity, and density perturbations is generally understood to go as a negative-exponent function of wavenumber (spatial periodicity)—sometimes very roughly characterized as $1/f^2$ or $1/f^{1.5}$. This fine structure goes down to millimeter scale and lower.

Although the second major aspect of the invention thus significantly advances the art, nevertheless to optimize enjoyment of its benefits preferably the invention is practiced in conjunction with certain additional features or characteristics. In particular, most of the same preferences mentioned above for the first facet are applicable here as well.

Also preferably the data-acquisition and -processing system is fabricated in a substantially unitary assembly with the sensors and includes circuits for deriving from the measurement signals secondary parameters of such liquid for the substantially identical measurement volumes.

A third primary aspect—In preferred embodiments of its third major independent facet or aspect, the invention apparatus includes a conductivity sensor for measuring electrical conductivity of such liquid, and a thermometer for measuring temperature of such liquid. Also included is a data-acquisition and -processing system connected to receive measurement signals from the conductivity sensor and thermometer, representing conductivity and temperature.

The data-acquisition and -processing system includes a circuit for modifying at least one of the measurement signals to remove signal artifacts due to detritus passing by or through the conductivity sensor or the thermometer. The foregoing may represent a description or definition of the third aspect or facet of the invention in its broadest or most general form. Even as couched in these broad terms, however, it can be seen that this facet of the invention importantly advances the art.

In particular, this aspect of the invention very greatly enhances the accuracy of derived parameters by, in yet another way, making the primary parameter values more rationally combinable with one another. It will be clear to those skilled in this field that detritus passing through or near the sensors affects temperature measurement in some entirely different manner than conductivity measurement—and even if this were not so, the values of speed of sound etc. for the detritus are most ordinarily not of interest.

To the extent that information about the detritus itself does happen to be of interest, this form of the invention is very straightforwardly configured to report all such data found in the conductivity and temperature measurement process. Thus operation of this facet of the invention is entirely beneficial and has no adverse effects.

Although the third major aspect of the invention thus significantly advances the art, nevertheless to optimize enjoyment of its benefits preferably the invention is practiced in conjunction with certain additional features or characteristics. In particular, the preferences noted earlier are also applicable to this third facet of the invention.

When this form of the invention is used with the liquid being ocean, estuarine, or brackish water, then preferably the apparatus includes mooring hardware or vehicles and mounting or towing hardware, as needed for positioning or moving the sensors through that water. Also preferably the circuit substitutes a signal representative of at least one period before or after the passing of the detritus, or both, in place of signal generated in response to the detritus.

A fourth primary aspect—In preferred embodiments of its fourth major independent facet or aspect, the invention apparatus includes two conductivity sensors for measuring electrical conductivity of such liquid; and at least one thermometer for measuring temperature of such liquid. It also includes a structural assembly for supporting the sensor and thermometer.

The assembly includes at least two circuit cards or ceramic cards having structural strength to provide mechanical integrity to the assembly. The cards are mutually disposed in a parallel, substantially aligned relationship and have the two conductivity sensors at mutually opposed faces of two of the cards.

The foregoing may represent a description or definition of the fourth aspect or facet of the invention in its broadest or most general form. Even as couched in these broad terms, however, it can be seen that this facet of the invention importantly advances the art.

In particular, this aspect of the invention provides a sensor-package configuration that presents a low aspect ratio and as such is very amenable to packaging and positioning through use of commonplace devices. In addition the unit offers very good flow dynamics for minimal fouling.

Although the fourth major aspect of the invention thus significantly advances the art, nevertheless to optimize enjoyment of its benefits preferably the invention is practiced in conjunction with certain additional features or characteristics. In particular, preferably the device also has third and fourth circuit cards or ceramic cards, and these too have structural strength to provide mechanical integrity to the assembly.

They are best disposed at substantially right angles to, and for structural interconnection between, the first-mentioned two cards. The four cards form a substantially rectangular or square frame, open at two ends for circulation of such liquid through the frame.

In one preferred embodiment the thermometer or thermometers include a resistance wire mounted across the frame. This wire is connected at its two ends to points on the frame respectively associated with the two conductivity sensors—one particularly beneficial arrangement being connection to centerpoints of the two conductivity sensors respectively.

Another preferred embodiment places the thermistor mounted at a centerpoint of concentric conductivity-sensing electrodes. Yet another uses, instead of the two added cards, pillar-type or like standoffs.

These, like the cards, have structural strength to provide mechanical integrity to the assembly, and are disposed at substantially right angles to, and for structural interconnection between, the two cards. In this configuration the two cards and the pillar-type standoffs form a substantially rectangular or square frame, generally open at four faces for circulation of the liquid.

Other preferences mentioned in regard to earlier-introduced aspects of the invention apply here as well. For concentric and other conductivity electrodes, the maximum dimension of each electrode is preferably about 1.5 centimeter.

A fifth primary aspect—In preferred embodiments of its fifth major independent facet or aspect, the invention apparatus includes at least one conductivity sensor for measuring electrical conductivity of such liquid, and at least one thermometer for measuring its temperature. Also included is circuitry connected to receive and manipulate electrical signals from the sensor and thermometer; and a common ceramic substrate holding the sensor, thermometer and circuitry.

The foregoing may represent a description or definition of the fifth aspect or facet of the invention in its broadest or most general form. Even as couched in these broad terms, however, it can be seen that this facet of the invention importantly advances the art.

In particular, the benefits of this fifth aspect of the invention go to manufacturability, economy, durability and reliability. All of these commercially vital characteristics are very greatly enhanced, relative to the prior art, by this facet of the invention.

Although the fifth major aspect of the invention thus significantly advances the art, nevertheless to optimize enjoyment of its benefits preferably the invention is practiced in conjunction with certain additional features or characteristics. In particular, preferably the thermometer is either a thermistor chip applied directly to a substrate holding the circuitry, or a thermistor bead mounted in a niche in the circuitry.

Preferably the circuitry includes an analog-to-digital converter digitizing the signals, memory means holding calibration coefficients for each sensor and each thermometer; and a data bus transmitting the signals with embedded calibration coefficients to a processing unit. The memory means may take any of a great number of forms that are equivalent for purposes of this invention—ROM, PROM, EPROM, and even in high-volume markets incorporation of critical information into an ASIC that operates the entire sensory package.

Preferably too the processing unit is programmed for plotting and data archiving. In most preferred cases the processing unit is disposed, remote from the sensor and thermometer, in a vehicle or shore facility; and the associated equipment there too forms an integrated part of this aspect of the invention.

When the thermometer is a thermistor, characteristically it will exhibit an asymptotic time-response function. In that case, preferably the circuitry also includes a module that executes a program for calculating a limit value from early response data.

A sixth primary aspect—In preferred embodiments of its sixth major independent facet or aspect, the invention apparatus includes a tube for passage of such liquid. It also includes at least one slot formed through a side wall of the tube.

A generally planar substrate is mounted in the slot, extending inward from the slot across the tube interior, and also extending outward from the slot and projecting from the tube. A conductivity sensor is formed on opposite sides of the portion of the substrate that extends across the tube interior, for measuring electrical conductivity of such liquid.

Also included is a thermometer for measuring temperature of such liquid. The foregoing may represent a description or definition of the sixth aspect or facet of the invention in its broadest or most general form. Even as couched in these broad terms, however, it can be seen that this facet of the invention importantly advances the art.

In particular, this configuration provides a particularly stable measurement that can be designed in such a way as to suffer minimal deterioration due to electrode erosion. This is due to the long conductivity-measurement path, in combination with relatively broad electrode surface, available in this configuration.

This configuration also offers good mixing, and presents an excellent location for positioning the thermistor relative to dual lobes of the conductivity cell if that particular design is selected. Other benefits of this particularly preferred form of the invention will appear from the details taken up later in this document.

Although the sixth major aspect of the invention thus significantly advances the art, nevertheless to optimize enjoyment of its benefits preferably the invention is practiced in conjunction with certain additional features or characteristics. In particular, preferably the conductivity sensor includes electrodes extending along the substrate and across the tube, on said opposite sides of the substrate.

In this case the electrodes advantageously include, on each side of the substrate, two generally parallel current-driving electrodes, and a sensing electrode generally parallel to and between the driving electrodes. Preferably the conductivity measurement paths extend through such liquid within and generally parallel to the tube—between the electrodes on one side of the substrate and the electrodes on the opposite side of the substrate—by passing around at least one edge of the substrate.

Also in this arrangement these paths include two paths, passing around two opposite edges of the substrate. These two paths now define two conductivity-measurement sensitivity lobes—extending in opposite generally axial directions within the tube—from the sensing electrode on one side of the substrate to the sensing electrode that is on the opposite side.

Preferably in this case the thermometer is mounted substantially between the two conductivity-measurement sensitivity lobes. In another subpreference, the thermometer includes two temperature sensors, one on each side of the substrate, each temperature sensor disposed substantially between the two conductivity-measurement sensitivity lobes. For the sixth aspect of the invention preferably the electrodes are silk-screened on the substrate, and preferably the tube is of alumina.

A seventh primary aspect—In preferred embodiments of its seventh major independent facet or aspect, the invention apparatus includes a conductivity sensor for measuring electrical conductivity of such liquid. This sensor has concentric annular electrodes.

Also included is a thermometer for measuring temperature of such liquid. The thermometer is disposed within an innermost of the annular electrodes.

The foregoing may represent a description or definition of the seventh aspect or facet of the invention in its broadest or most general form. Even as couched in these broad terms, however, it can be seen that this facet of the invention importantly advances the art.

In particular, this configuration offers a classical collocation in which the most intense sensitivities of the two sensors are very well registered. Accordingly this simple and readily manufactured form of the invention is capable of high accuracy in the derived parameters.

Although the seventh major aspect of the invention thus significantly advances the art, nevertheless to optimize enjoyment of its benefits preferably the invention is practiced in conjunction with certain additional features or characteristics. In particular, many of the variants and preferences taught with regard to earlier-introduced aspects of the invention are generally applicable here as well.

An eighth primary aspect—In preferred embodiments of its eighth major independent facet or aspect, the invention is a process for manufacturing apparatus for measuring liquid conductivity. This process includes the step manufacturing a conductivity sensor that provides good measurement characteristics for any one of multiple different measurement applications.

The process also includes providing a circuit substrate that is compatible with the sensor and with any of the multiple different measurement applications. In addition, this method also includes the step of selecting a circuit configuration, for use with the sensor, from multiple different circuit configurations associated with the multiple measurement applications respectively.

Next the process includes the step of causing the selected circuit configuration to be formed on the substrate and interconnected with the sensor. Also included is the step of encapsulating the circuit and substrate.

The foregoing may represent a description or definition of the eighth aspect or facet of the invention in its broadest or most general form. Even as couched in these broad terms, however, it can be seen that this facet of the invention importantly advances the art.

In particular, the eighth aspect of the invention enables the manufacturer to very easily and quickly prepare a device that is custom-adapted to a new application that has just for the first time appeared—and to do so with excellent economics for both the manufacturer and the customer. After the first provision of a suitable circuit for any particular application, the photo masters for making that circuit can in effect be simply added to the manufacturer's library of circuitry for different applications. That application thereafter can be serviced with the preestablished excellent reliability of the overall package, and essentially the same low price as for earlier-introduced applications.

All of the foregoing operational principles and advantages of the present invention will be more fully appreciated upon consideration of the following detailed description, with reference to the appended drawings, of which:

BRIEF DESCRIPTION OF THE DRAWINGS

FIG. 5 is a side elevation of a sensor head in another prior-art conductivity and temperature measuring system, also showing inadequate collocation of two sensors;

FIG. 6 is a top plan of the FIG. 5 sensor head, drawn partly in the broken line to show the thermistor mounting within;

FIG. 7 is a bottom plan, but taken at an angle along the lines 7—7 in FIG. 5, to show the conductivity sensor face-on;

FIG. 8 is a perspective or isometric view of a combination measuring system, according to preferred embodiments of the present invention—and showing conductivity, temperature and pressure sensors mounted together with data-acquisition and data-processing functions, as well as enclosure of the temperature and conductivity sensors within a common liquid-flow chamber;

DETAILED DESCRIPTION OF THE PREFERRED EMBODIMENTS

Figure 1:
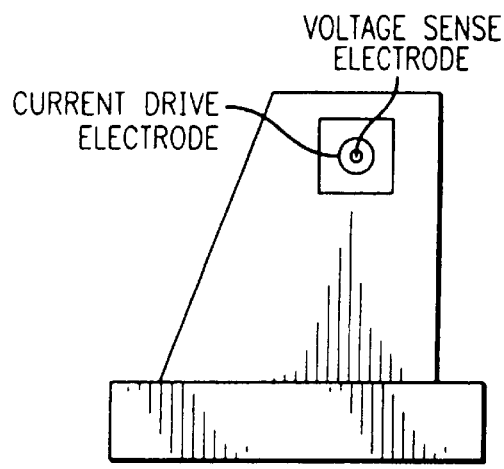
FIG. 1 is an elevational view, somewhat schematic, of a prior-art conductivity sensor previously developed by the present inventors.

In preferred embodiments of the invention, measurements are made with sensor technology that, by design, can be mass produced at low cost—yet achieves performance which is the same as or significantly superior to that currently available. The same basic sensor design is capable of use in a variety of ways including, merely by way of example, vehicle towing, mooring, submerged positioning, and cast probes.

Some characteristics of the previously mentioned technology developed by the present inventors for CTD sensors are incorporated in preferred embodiments of the present invention. By using ceramic circuit-board technology the inventors have found a way to inexpensively fabricate the electrodes for the conductivity cell and collocate the thermistor within its cell geometry.

In this regard the invention is unique among nonexpendable CTDs. As a result, collocation is much better than that in the one expendable commercial probe discussed earlier.

Like some of the earlier conductivity cells, the present invention uses a closed geometry, maximizing d. c. stability. The invention, however, diverges in that it does easily lend itself to mass production, by virtue of the particular electrode geometry that is favored.

As will be seen, the preferred configuration is in effect somewhat hybrid—employing an open, planar geometry for the electrodes as formed on their substrate, but then positioning that submodule bodily within an enclosure. This avoids the common methods for placing or forming electrodes on the inside of a tube, and thereby essentially avoids handcrafting techniques and their undesirable cost.

As mentioned earlier, previous expendable devices have relied on probe drop rate to account for depth. To achieve better accuracy for depth measurements, ideally a collocated pressure sensor is included in the present invention.

Preferred embodiments of this invention use a microelectromechanical machines (HEMS) transducer as the pressure sensor—preferably embedded in a common chip that provides the integrated data-acquisition and -processing subsystem. This pressure transducer is required for moored, vehicle-mounted, or towed applications, and is a great improvement over standard technology in the expendable probe.

This type of pressure transducer has accuracy limitations, but it is much better than the probe-drop technique. Collocation for the pressure sensor is not as important as for the other sensors, because in the most common measurement environments the ocean pressure gradients are not great enough—relative to the dimensions of the sensor—to cause significant derived-parameter error.

This is particularly true in view of the usual use of the pressure as independent variable; i. e., conductivity and temperature are most commonly considered as a function of depth (pressure). Thus the pressure measurement leads to establishing an independent position along an abscissa of a functional graph. Those of ordinary skill in the art, however, will understand that pressure gradients and collocation may be much more important in less commonplace measuring environments—such as for example measurement in industrial process control streams, or geothermal plants.

These embodiments use a ceramic substrate, like that previously mentioned as part of certain earlier conductivity sensors. The substrate is mounted to the sensor body with the sensing elements exposed and with encapsulation protecting the rear portion—which contains a multichip module (MCM) and power circuitry.

The water- and pressure-proofing encapsulation is preferably tailored to the specific use of the sensor platform. For expendable devices, the encapsulation need only last for the length of the probe drop, but must be packaged so that the circuitry withstands the pressures at 1000 meters depth. For moored, hard-mounted, or towed applications, the sensor must be capable of withstanding longer exposure to salt water.

Both these degrees of robustness are well within the state of the art, and their satisfactory performance by the present invention is entirely certain. In particular, as to the latter group of applications the relevant sensor technologies have proven reliable in several development programs over the last twenty years.

The invention provides accurate low- or high-frequency conductivity measurements collocated with a matched temperature sensor. In certain embodiments, it is feasible to reduce opposed conductivity electrode sizes to on the order of one centimeter, whereby high-frequency measurements can be obtained in an open planar or opposed-electrode configuration. This advancement not only permits accurate determination of the derived quantities—salinity, density and sound speed (and depth in applications with strong pressure gradients)—but also permits sensor devices to be mass-produced inexpensively, rather than built by costly handcrafted methods used heretofore.

To yield precise and accurate depth measurements, a miniature pressure transducer is included. The microelectromechanical machine (MEMS) depth sensor incorporated into the invention is useful in drop procedures and required in many moored, bottomed, vehicle-mounted, or towed applications. The circuitry within the MCM costs little, requiring a frequency decoder, built straightforwardly as another channel in the MCM.

Another direct benefit due to the integrated configuration of preferred embodiments of the present invention is the number of different applications and embodiments it can take. The sensor is small enough to fit within a towed array, or to seed a littoral zone, or to be hard-mounted to autonomous platforms without using up as much precious volume or consuming as much power as previous sensing systems.

The invention is very readily adapted to sensing of other or additional parameters—in many cases simply by changing out the circuit that is formed in the assembly—making it a very flexible, capable measurement platform.

As suggested earlier, the technology exists to have the sensing elements and the circuitry carried together on the same ceramic substrate. The invention may use a temperature sensor in the form of a thermistor, or platinum resistance thermometer, or other suitable unit.

Thermistor elements have existed for years in chip form that can be directly applied to a circuit board. This type of mounting is particularly useful in some applications to provide collocation of the temperature sensor with the conductivity device; such surface-mount configurations, however, require careful attention with respect to bandwidth matching.

Figure 9:
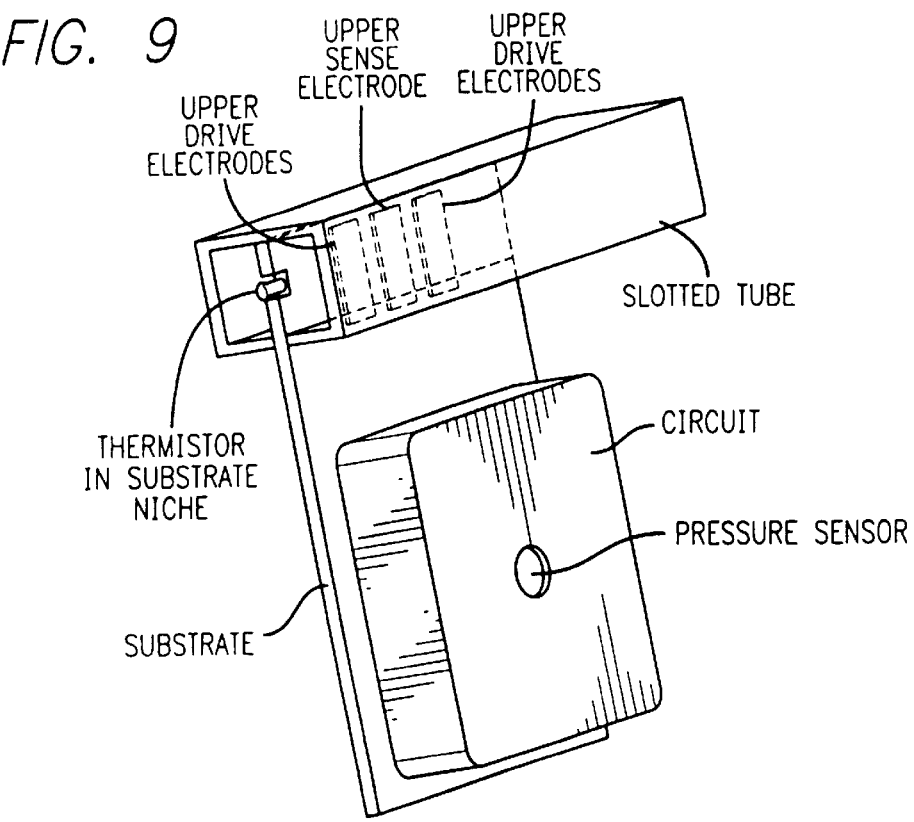
FIG. 9 is a like view of alternative preferred embodiments of the system of the invention, having circuit elements at only one side of the tube.
Figure 12:
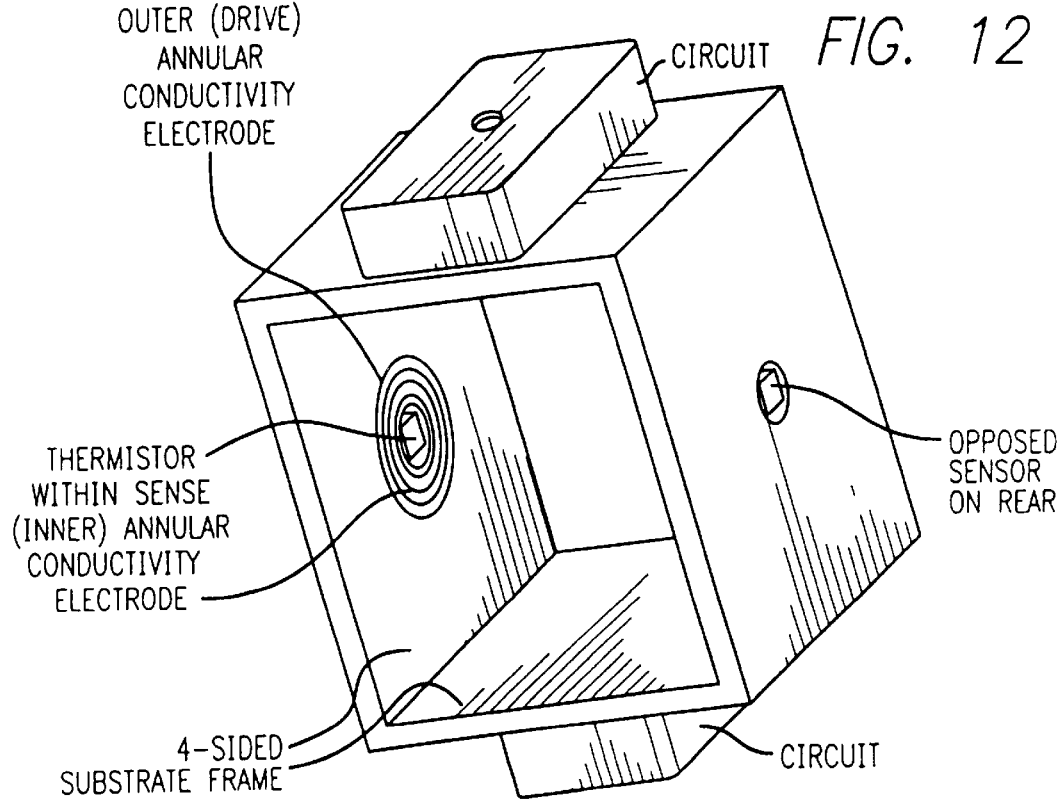
FIG. 12 is a like view of a square or cubical embodiment of the system of the invention, formed with four substrate or circuit cards—not showing yet another embodiment using flex circuit cards and standoffs.
Figure 13:
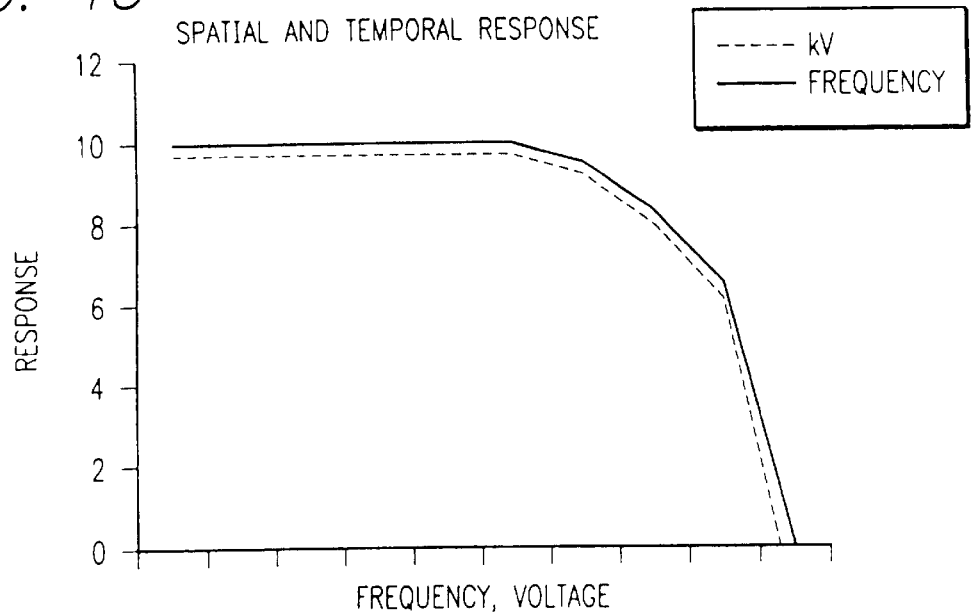
FIG. 13 is a diagram very conceptually showing representative spatial and temporal bandwidths of the two collocated sensors of the FIGS. 8 through 12 embodiments, as contemplated by the present invention.
Figure 14:
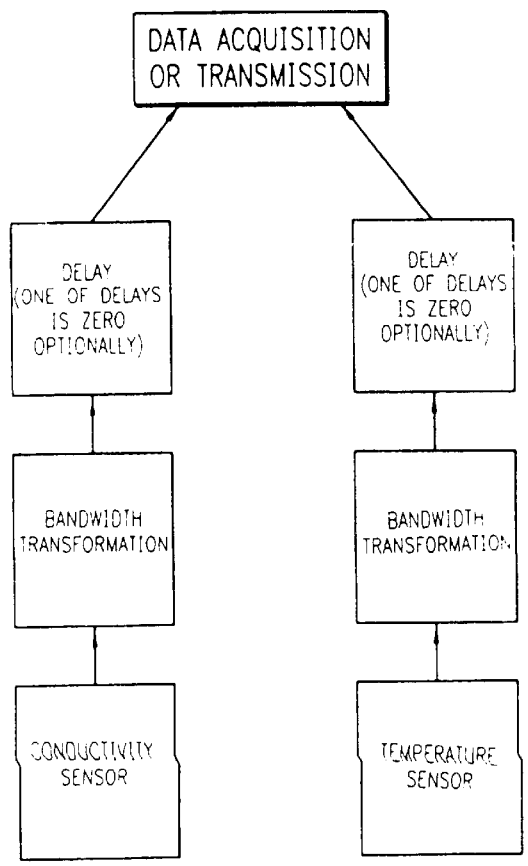
FIG. 14 is an electronics block diagram for a signal filter arrangement which converts the measured signals (one or both) from the raw measured bandwidths into some selected identical bandwidth, and also (in either order) retards at least one of the same-bandwidth signals so that the two signals are synchronized.
Figure 15:
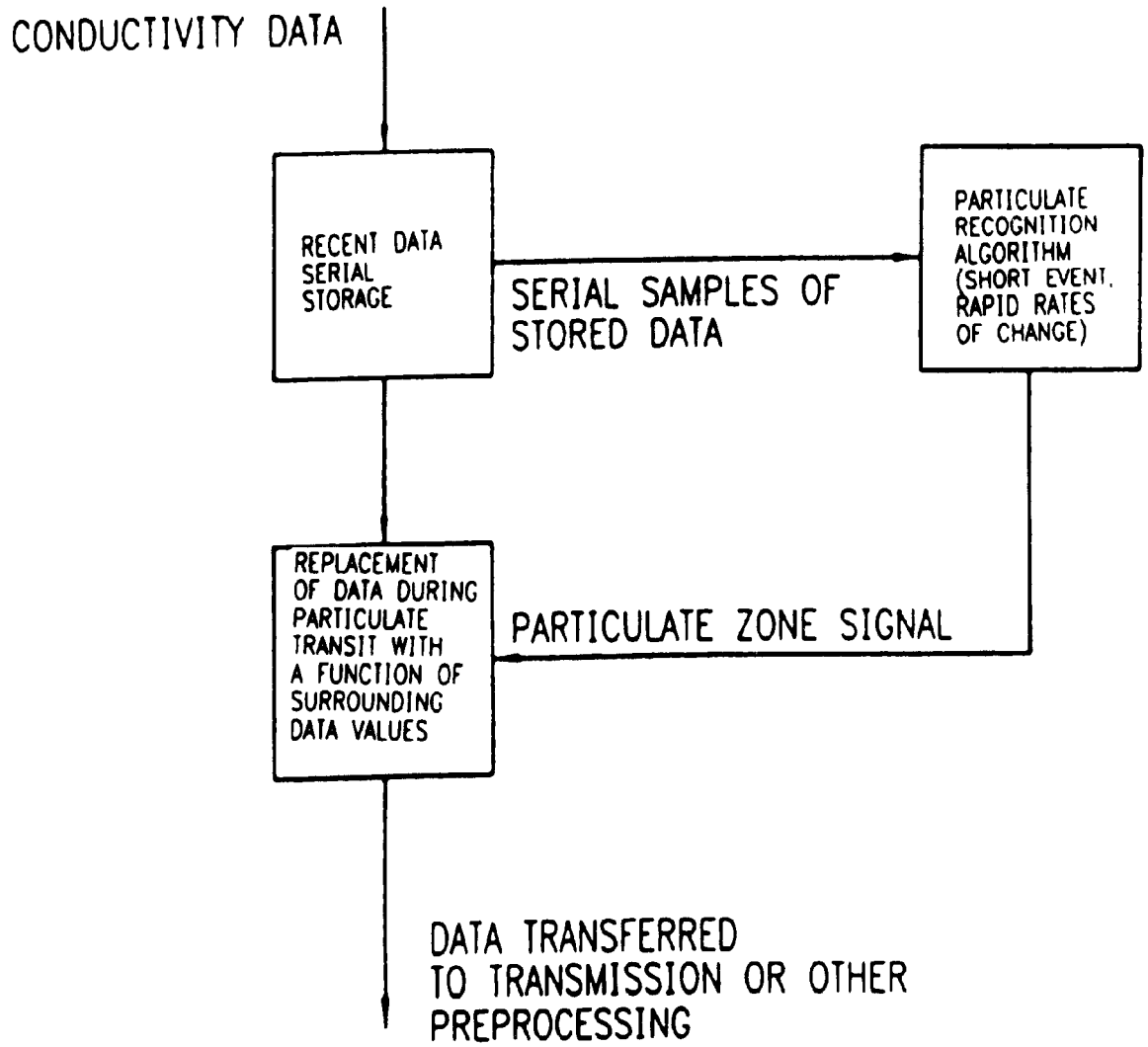
FIG. 15 is a like diagram of a nonlinear filter that eliminates signal fluctuations which cannot represent real conductivity fluctuations but would be generated by particulates passing through the sensor.
Figure 16:
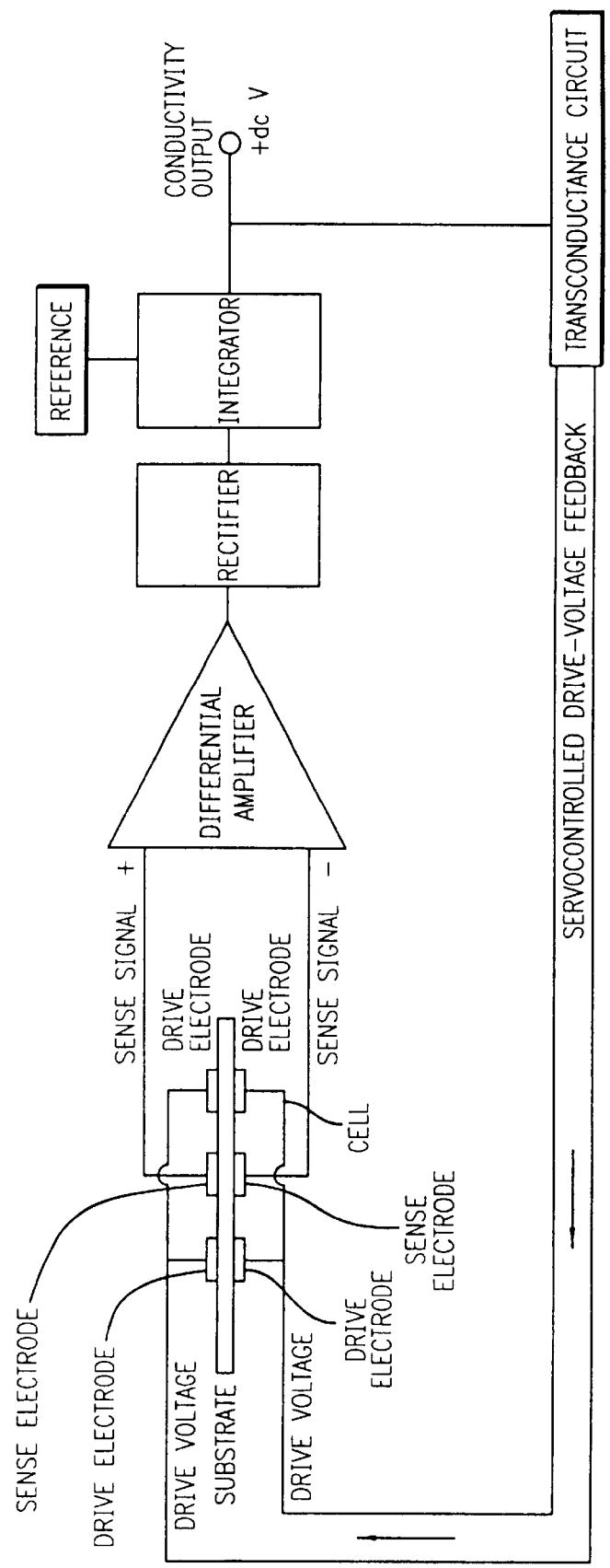
FIG. 16 is a schematic diagram, at a conceptual level, of the conductivity-sensor analog electronics (the blocks of FIGS. 14 and 15 may be incorporated at any of various points in this schematic; signals at essentially all points are square-wave).

Otherwise a niche-mounted separate preencapsulated thermistor unit (FIGS. 8–9) is readily employed instead—though at notably increased cost. The surface-mount approach is particularly preferable if resolution of 2 m or more is acceptable, and the niche-mount advisable for resolutions of about 1 m and finer.

According to preferred embodiments of the invention, the temperature sensor is positioned within the spatial sensing volume of a conductivity sensor, allowing both sensors to sample a substantially identical volume of water. The effective measurement volumes of the two sensors are respectively shown in FIG. 2.

For concentric-electrode conductivity sensors, a particularly advantageous configuration includes replacing a central "dot"-shaped conductivity electrode with an annular electrode of like outer diameter. The temperature sensor is then disposed within that annulus.

As to temperature, the achieved results mentioned in the background section are available for combination with the present configuration and are much better than the available commercial unit. A preferable approach for many applications, however, is instead to degrade these specifications and thereby help make practice of the invention easy and economical.

The temperature sensor requires encapsulation under, for example, glass to isolate it electrically from seawater or other corrosive measuring environments. The glass coating must be thin enough, however, to measure the temperature of the surrounding water, not that of the ceramic substrate or its surrounding glass.

Such provisions help to preserve the spatial and temporal resolution of the temperature measurements—and their collocation with the conductivity and pressure measurements. From this kind of example, those skilled in the art will appreciate other ways in which the collocation, bandwidth matching and synchronization can be enhanced.

Operation of this part of the invention is assured because various commercial thermistor vendors have optimized the glass insulation for the thermal time constant and electrical isolation properties. Application of glass coatings on ceramic circuit cards is essentially standard, using the same silk-screening techniques used to form multiple layers within the ceramic substrate.

Those skilled in the art will appreciate that temperature sensors in accordance with the principles of the present invention can take a very great number of forms. For instance, it is not required to limit the quantity of sensors to just one or two; rather, multiple temperature sensors in many different sorts of arrays can be used.

Resistance wires can be used. The temperature sensing function can be distributed, for instance formed on an entire wall of a combination sensor assembly. Other techniques based on the teachings set forth in this document will suggest themselves.

The conductivity-electrode subsystem of the present invention is an improvement—emphasizing manufacturing cost reduction—of the earlier-discussed known prior conductivity sensor developed previously by the present inventors using thick-film silkscreening techniques. The principle of this module has been demonstrated, but its configuration in the present invention is novel.

With the savings potential in the present invention, a selling price at least one-quarter less than that of the XCTD, and possibly as low as that of the XBT, is contemplated. This pricing capability greatly increases the potential user base and usefulness of the XCTD probe The backbone of preferred embodiments of this sensor system is a multilayer ceramic circuit card doubling as the platform to carry the sensing elements. Using this technique makes the sensor very cost effective, since the sensor and electronics are contained on the same robust, small, mass-reproducible platform.

Ceramic is inert in seawater, is easy to encapsulate and has compression coefficients easily matched to the other materials required to make the sensor function at ocean depths. The techniques required for fabrication of the temperature and conductivity sensors are well known in the art.

One embodiment of the sensor circuitry optimizes for a low input power requirement and relatively high absolute accuracy. Compared to the previous devices used for high band-width and high sensitivity, the sensor electronics here draws much less current thereby reducing electrode erosion. The time-tested constant-voltage-servo approach may be used to make the conductivity electronics.

The invention collocates the temperature and conductivity sensing elements within the flow channel of the conductivity cell. This configuration alleviates the errors and data-processing problems associated with deriving the seawater density and sound speed from noncomparable or inadequately compatible primary sensor measurements.

This innovative design feature ensures that both sensors sample the same water volume. To achieve this goal, the temperature sensor thermistor is placed on the ceramic substrate in the sampling volume of the conductivity cell. Key design parameters incorporated to produce an effective temperature sensor are:

- materials choice (thermal expansion and mechanical compression coefficient matching)—a preferable form, at the present writing, being a glass-encapsulated thermistor, surface-mount chip thermistor, thick-film thermistor, or platinum resistance thermometer;
- thermistor chip choice (response time of encapsulated chip, in relation to probe flow rate)—some currently preferred chips being Thermometrics model P30 glass-encapsulated thermistor with maximum diameter of 0.030 inch, or type FM thermochip unencapsulated rectangular model with maximum dimensions of 0.020 inch on each side and 0.003 to 0.005 inch thickness; and thermistor circuit design (self-heating vs. resolution)—current preferences at this time including bridges or half-bridges built in ratiometric analog or digital circuits.

The P30 is best chosen with standard length of 0.125 inch. The "plunge in water" thermal time constant is 60 msec, which is advantageous (even though faster and slower units are readily available) because it enables matching response to that of the best preferred conductivity sensor—for, e. g. a 0.5 to 1 m overall instrument vertical resolution. The P30 has correct time constant for bandwidth matching, and is large enough for mechanical sturdiness.

The preferred model of the FM offers a 100 kΩ resistance at 25° C., requires addition of external encapsulation, and mounts flat, directly to a circuit board or card such as used in certain preferred embodiments of the invention. As this unit is extremely thin, it can yield a suitable time constant when encapsulated and mounted—the time constant being in effect that of the encapsulation and mounting.

A particularly favorable embodiment of the conductivity-cell electrodes is fabricated by silkscreening a predetermined electrode pattern on both sides of a preferably generally planar ceramic substrate. This sensor is completed at the final probe assembly by inserting the edge of the ceramic substrate through slots formed in opposing walls of an electrically nonconducting tube of e. g. alumina, and bonding the seams.

Figure 2:
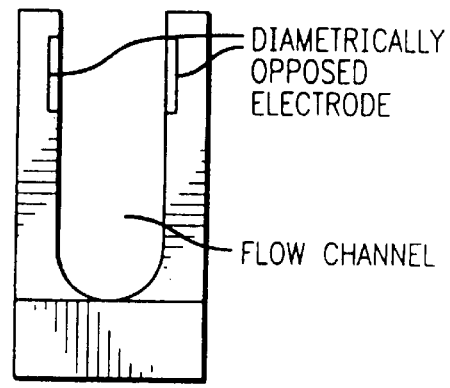
FIG. 2 is a like end view of the FIG. 1 sensor.
Figure 10:
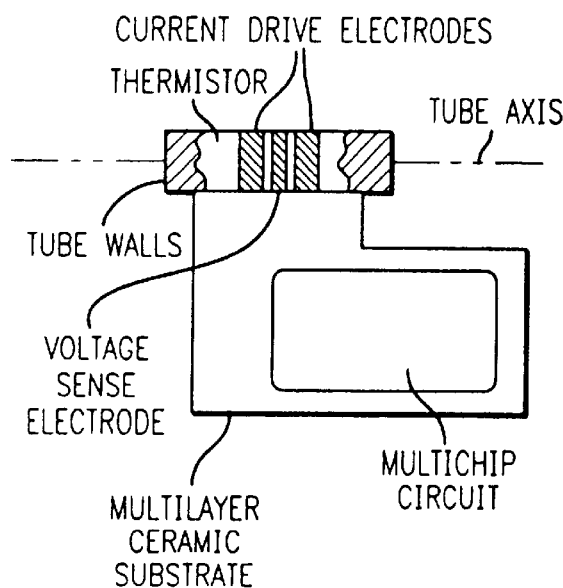
FIG. 10 is a side elevation of the FIG. 9 system.
Figure 11:
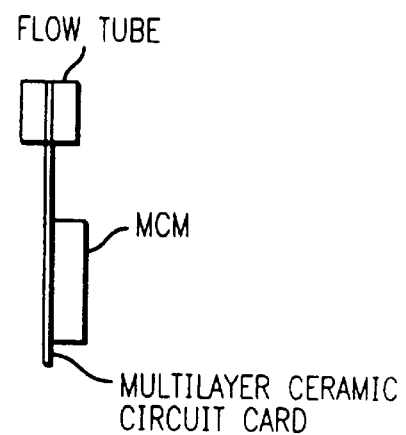
FIG. 11 is an end elevation of the same system.
Figure 3:
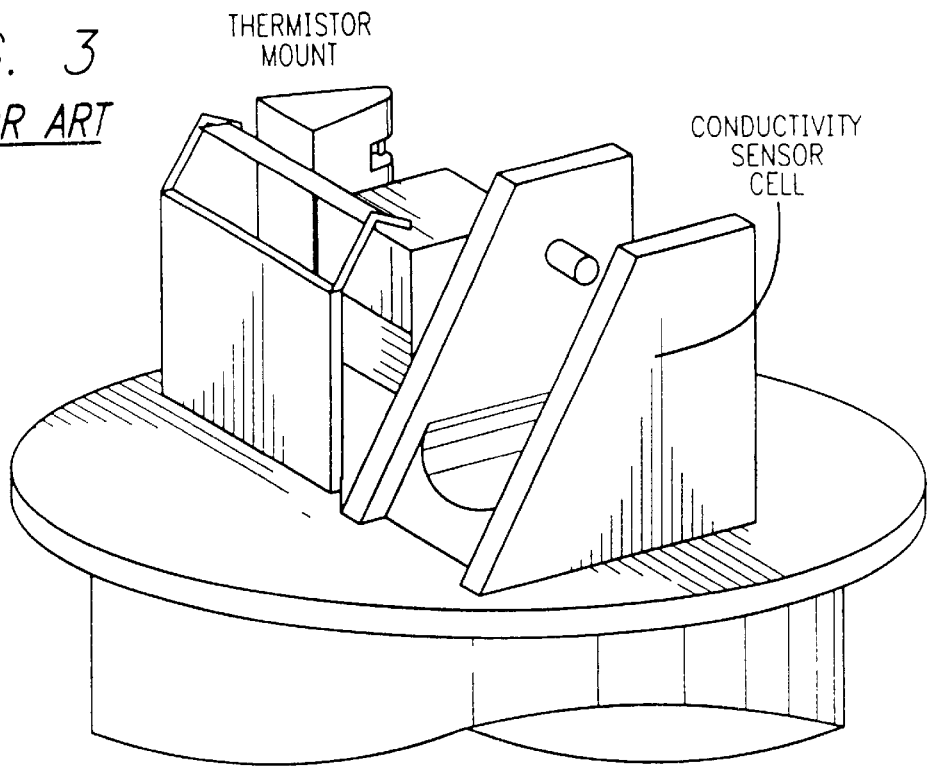
FIG. 3 is a perspective view, taken from the front and to one side, of the same sensor.
Figure 4:
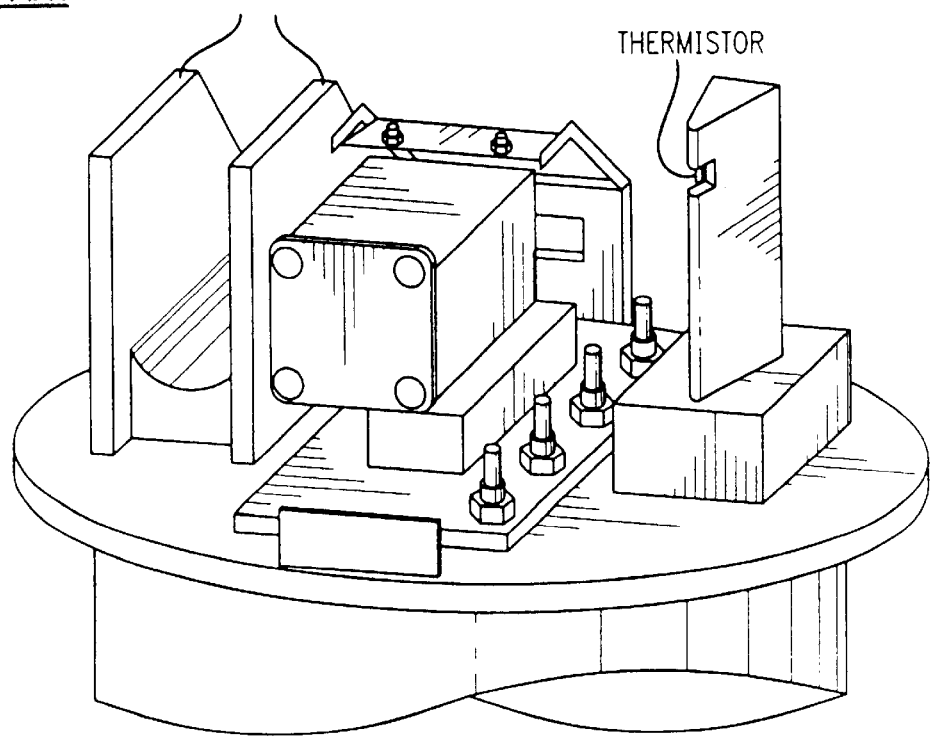
FIG. 4 is a like view of the same sensor from the rear, together with an associated temperature sensor—in a likewise prior-art system that was associated with the FIG. 1 sensor—and also showing inadequate collocation of the conductivity and temperature sensors; the view further includes apparatus for transmission of sensor signals to remote data-acquisition and remote data-processing functions.

Preferably the generally planar substrate very generally bisects the tube (FIG. 2). The resultant conductivity sensor is very stable and reproducible.

The current-drive electrodes are shown as the two outer stripes on each side of the ceramic. (Only the upper set of stripes is shown explicitly; the lower set is shown implicitly, being substantially identical.) The center stripe on each side is the voltage-sensing electrode.

Current is driven from each outboard stripe through the flowing water to (primarily) the nearer edge of the ceramic substrate card, and around to its opposite counterpart on the opposite side of the substrate. This geometry positions the sensing (voltage) electrodes in a very stable isopotential region—which in some configurations also provides one ideal location for the thermometer.

The circuitry servocontrols the voltage across the sensing electrodes to a constant level. The current driven to maintain that level is directly proportional to the conductivity of the water in the surrounding cell.

The sensor output is digitized and transmitted on a data bus with embedded calibration coefficients for each probe. The requirements for data acquisition from the sensors into a vehicle, shore facility etc. are reduced to a software program for plotting and data archiving, another potential cost saving.

The sensor units can be produced in quantity without custom fitting. With quality control in the silkscreen printing of the thick-film inks, all production conductivity cells can be made, for practical purposes, dimensionally identical.

The platinization required on the conductivity sensors is done in batches before final sensor assembly. Tailoring of the gains of the circuits within each MCM is done on an automated tester. Batch calibration of the sensor remains the only manual operation.

Developing cell geometries within tubes yields a more stable cell for low-frequency measurements, but increases the risk of fouling or clogging. For expendable devices the increased risk of fouling is a minor factor, but the conductivity sensor must be stable from the instant of immersion. This requires prewetting of the electrode surfaces for the removal of microbubbles in the platinized cell. Corks mounted to each side of a tube-configured unit enable prewetting conveniently. For towed or longer-term deployments, while fouling of the sensor with detritus must be addressed, using an opposed planar cell embodiment opens the geometry enough to avoid adherence of such materials to the opposed planes; closed geometry would run the risk of clogging.

The measurement accuracy needed requires that the circuitry of the temperature and conductivity sensors be stable over long periods of time and at various temperatures to well better than one part per thousand. The requisite levels of stability can be achieved with careful design and with high-quality components placed on the ceramic sheet on which the conductivity electrodes are deployed.

Other embodiments of conductivity cell design such as shown in FIG. 1 are applicable if longterm use of the sensor is required. The ceramic circuit board also provides space for self-contained power sources for expendable or short-term operations.

As pointed out earlier, a primary objective of this invention is manufacturing economy. For this reason it is preferred to implement the invention in configurations that can be manufactured in ways that are as economical as feasible.

The invention emphasizes the equivalence of the sampling volumes of the temperature and the conductivity sensors. This equivalence is achieved primarily by making the fluid volumes seen by the two sensors be as nearly as practical the same volume—as distinguished from, for example, offset volumes or even nested volumes.

The semantic difficulties of quantifying this highly desired collocation principle have been introduced earlier. Although the words are difficult, those of ordinary skill in the art will find that it is not difficult to apply the principle very effectively to practical cases—e. g., to practical candidate configurations.

Notwithstanding these important principles of the invention, as a practical matter the temperature sensor is instead ordinarily within some subset of the conductivity-cell volume. Similarly, the temporal behavior of heat flow to and within the temperature sensor typically is slightly different from the temporal behavior of fluid flow through and contacting the conductivity cell.

Thus there may remain small delays between the two sensor outputs, and there may remain slight differences in bandwidth. The invention includes provision of electrical filters or near-front-end firmware/software processing—or other means, as appropriate to the measuring environment and production economics—to further transform the electrical outputs of the conductivity and temperature sensors. Thus for example in very high production volumes the data handling can be performed with excellent economy and speed by an application-specific integrated circuit (ASIC).

These provisions account for delays and compensate for residual bandwidth differences (FIGS. 6 and 7). In addition these features of the invention can be used to eliminate some undesirable characteristics of the sensing hardware. For instance thermistors have an asymptotic response function, and it is straightforward to calculate the limit value from early response. Those of ordinary skill in this field can program the system to fit an exponential function to the early-response curve, and thereby eliminate long waits for the final result.

Preferred embodiments also include provision for removing errors caused by particulates in the water passing through the cell. This means involves circuitry or digital procedures within the sensor system that recognize rapid variations in perceived conductivity that are not characteristic of sea water but are characteristic of passing particulates.

In response to such recognition, the region of data contaminated by a particulate is replaced in the data stream by typical values computed from the immediately surrounding time (FIG. 8). For instance, the several data points acquired during passage of each particle or slug of particulate matter are advantageously replaced with a representative (e. g. average) value of the data stream during the immediately preceding or immediately following samples, or both.

The invention is not limited to use with saline water or aqueous liquids, although these may encompass the most common applications. Uses include monitoring of estuarine and other brackish water, powerplant outflows, and industrial-plant liquids (e. g. juices), or industrial discharges, or water in geothermal plants. Other important applications include monitoring of process streams, sulfur and other mineral extraction, geological exploration.

In general monitoring of different liquids requires different parameters in the circuitry—but to a much lesser extent in the sensors. Thus an important benefit of the invention is that the sensor geometries prescribed are substantially stable across applications. Widely different uses are implemented with only changes in the specific circuit that is formed in the sensor assembly.

It will be understood that the foregoing disclosure is intended to be merely exemplary, and not to limit the scope of the invention—which is to be determined by reference to the appended claims.

What is claimed is:

1. Apparatus for determining parameters of a liquid; said apparatus comprising:
   a conductivity sensor for measuring electrical conductivity of such liquid;
   a thermometer for measuring temperature of such liquid; and
   a data-acquisition and -processing system connected to receive measurement signals from the conductivity sensor and thermometer, representing conductivity and temperature;
   the data-acquisition and -processing system comprising a circuit modifying at least one of the measurement signals to remove signal artifacts due to detritus passing by or through the conductivity sensor or the thermometer.

2. The apparatus of claim 1, wherein:
   the data-acquisition and -processing system is a substantially unitary assembly with the sensors and comprises circuits deriving from said measurement signals secondary parameters of such liquid.

3. The apparatus of claim 2, wherein:
   the secondary parameters comprise density of such liquid and speed of sound in such liquid.

4. The apparatus of claim 2, further comprising:
   a pressure sensor for determining pressure of such liquid; and wherein:
   the data-acquisition and -processing system further receives pressure-measurement signals from the pressure sensor representing values of pressure that are associated with values of conductivity and temperature measured by the conductivity sensor and thermometer; and
   the data-acquisition and -processing system further derives, from said pressure-measurement signals, depth of such liquid.

5. The apparatus of claim 4, wherein:
   the pressure sensor is a MEMS transducer.

6. The apparatus of claim 5, wherein:
   the transducer is embedded in a common chip that provides the data-acquisition and -processing system.

7. The apparatus of claim 1, for use with said liquid being ocean, estuarine, or brackish water; and further comprising:
   hardware for mooring the sensors in, or a vehicle and associated hardware for vehicle-mounting them in or towing them through such ocean, estuarine or brackish water.

8. The apparatus of claim 1, wherein:
   the signal-modifying means comprise means for substituting a signal representative of at least one period before or after the passing of the detritus, or both, in place of signal generated in response to the detritus.

9. The apparatus of claim 8, wherein:
   the substituting means comprise a circuit.

10. Apparatus for determining parameters of a liquid; said apparatus comprising:
    two conductivity sensors for measuring electrical conductivity of such liquid; and
    at least one thermometer for measuring temperature of such liquid; and
    a structural assembly for supporting the sensor and thermometer, said assembly comprising at least two circuit cards or ceramic cards having structural strength to provide mechanical integrity to the assembly and mutually disposed in a parallel, substantially aligned relationship and having the two conductivity sensors at mutually opposed faces of two of said cards.

11. The apparatus of claim 10, further comprising:
    third and fourth circuit cards or ceramic cards also having structural strength to provide mechanical integrity to the assembly and disposed at substantially right angles to, and for structural interconnection between, the first-mentioned two cards;
    the four cards forming a substantially rectangular or square frame open at two ends for circulation of such liquid therethrough.

12. The apparatus of claim 11, wherein:
    the at least one thermometer comprises a resistance wire mounted across the frame.

13. The apparatus of claim 12, wherein:
    the resistance wire is connected at its two ends to points on the frame respectively associated with the two conductivity sensors.

14. The apparatus of claim 11, wherein:
    at least one of the two conductivity sensors has concentric electrodes; and
    the at least one thermometer comprises a thermistor mounted at a centerpoint of the concentric electrodes.

15. The apparatus of claim 10, wherein:
    the at least one thermometer comprises a resistance wire mounted across the frame.

16. The apparatus of claim 15, wherein:
    the resistance wire is connected at its two ends to points on the frame respectively associated with the two conductivity sensors.

17. The apparatus of claim 16, wherein:
    the resistance wire is connected at its two ends to centerpoints of the two conductivity sensors respectively.

18. The apparatus of claim 10, further comprising:
    pillar-type standoffs also having structural strength to provide mechanical integrity to the assembly and disposed at substantially right angles to, and for structural interconnection between, the two cards;

the two cards and the pillar-type standoffs forming a substantially rectangular or square frame, generally open at four faces for circulation of such liquid therethrough.

19. The apparatus of claim 18, wherein:
the at least one thermometer comprises a resistance wire mounted across the frame.

20. The apparatus of claim 19, wherein:
the resistance wire is connected at its two ends to points on the frame respectively associated with the two conductivity sensors.

21. The apparatus of claim 19, wherein:
the resistance wire is connected at its two ends to centerpoints of the two conductivity sensors respectively.

22. The apparatus of claim 18, wherein:
at least one of the two conductivity sensors has concentric electrodes; and
the at least one thermometer comprises a thermistor mounted at a centerpoint of the concentric electrodes.

23. The apparatus of claim 10, wherein:
the maximum dimension of each conductivity electrode is 1.5 centimeter.

24. Apparatus for determining parameters of a liquid; said apparatus comprising:
at least one conductivity sensor for measuring electrical conductivity of such liquid; and
at least one thermometer for measuring temperature of such liquid,
circuitry connected to receive and manipulate electrical signals from the sensor and thermometer; and
a common ceramic substrate holding the sensor, thermometer and circuitry, said thermometer comprising a thermistor chip applied directly to the substrate holding the circuitry.

25. The apparatus of claim 24, wherein the circuitry comprises:
an analog-to-digital converter digitizing the signals;
memory means holding calibration coefficients for each sensor and each thermometer;
a data bus transmitting the signals with the calibration coefficients embedded therein to a processing unit.

26. The apparatus of claim 25, wherein:
the processing unit is programmed for plotting and data archiving.

27. The apparatus of claim 25, wherein:
the processing unit is disposed, remote from the sensor and thermometer, in a vehicle or shore facility.

28. The apparatus of claim 24:
wherein the thermometer is a thermistor, having an asymptotic time-response function; and
the circuitry comprises a module that executes a program for calculating a limit value from early response data.

29. Apparatus for determining parameters of a liquid; said apparatus comprising:
at least one conductivity sensor for measuring electrical conductivity of such liquid; and
at least one thermometer for measuring temperature of such liquid;
circuitry connected to receive and manipulate electrical signals from the sensor and thermometer; and
a common ceramic substrate holding the sensor, thermometer and circuitry; and
wherein the thermometer is a thermistor bead mounted in a niche in the substrate.

30. Apparatus for determining parameters of a liquid; said apparatus comprising:
a tube for passage of such liquid therethrough;
at least one slot formed through a side wall of the tube;
a generally planar substrate mounted in the slot and extending inward from the slot across the tube interior, and also extending outward from the slot and projecting from the tube;
a conductivity sensor, formed on opposite sides of the portion of the substrate that extends across the tube interior, for measuring electrical conductivity of such liquid; and
a thermometer for measuring temperature of such liquid.

31. The apparatus of claim 30, wherein:
the conductivity sensor comprises electrodes extending along the substrate and across the tube, on said opposite sides of the substrate.

32. The apparatus of claim 31, wherein:
the electrodes comprise, on each side of the substrate, two generally parallel current-driving electrodes, and a sensing electrode generally parallel to and between the driving electrodes.

33. The apparatus of claim 32, wherein:
conductivity measurement paths extend through such liquid within and generally parallel to the tube, between the electrodes on one side of the substrate and the electrodes on the opposite side of the substrate, by passing around at least one edge of the substrate.

34. The apparatus of claim 33, wherein:
the paths comprise two paths passing around two opposite edges of the substrate; and
said two paths define two conductivity-measurement sensitivity lobes extending in opposite generally axial directions within the tube from the sensing electrode on one side of the substrate to the sensing electrode that is on the side opposite said one side.

35. The apparatus of claim 34, wherein:
the thermometer is mounted substantially between the two conductivity-measurement sensitivity lobes.

36. The apparatus of claim 34, wherein:
the thermometer comprises two temperature sensors, one on each side of the substrate, each temperature sensor disposed substantially between the two conductivity-measurement sensitivity lobes.

37. The apparatus of claim 30, wherein:
the electrodes are silkscreened on the substrate.

38. The apparatus of claim 30, wherein:
the tube is of alumina.

39. Apparatus for determining parameters of a liquid; said apparatus comprising:
a conductivity sensor for measuring electrical conductivity of such liquid, the sensor having concentric annular electrodes; and
a thermometer for measuring temperature of such liquid, the thermometer being disposed within an innermost of the annular electrodes.

40. Apparatus for determining parameters of a liquid; said apparatus comprising:
a conductivity sensor for measuring electrical conductivity of such liquid;
a thermometer for measuring temperature of such liquid; and
a data-acquisition and -processing system connected to receive measurement signals from the conductivity sensor and thermometer, representing conductivity and temperature;

the data-acquisition and -processing system comprising means for modifying at least one of the measurement signals to remove signal artifacts due to detritus passing by or through the conductivity sensor or the thermometer.

41. The apparatus of claim 40, wherein:

the signal-modifying means comprise a circuit.

42. The apparatus of claim 40, wherein the data-acquisition and -processing system is a substantially unitary assembly with the sensors, and comprises means for deriving from said measurement signals secondary parameters of such liquid.

43. The apparatus of claim 42, wherein:

the deriving means comprise circuits.

44. The apparatus of claim 40, for use with said liquid being ocean, estuarine, or brackish water; and further comprising:

means for mooring the sensors in, or means for vehicle-mounting them in or towing them through such ocean, estuarine or brackish water.

45. The apparatus of claim 44, wherein:

the mooring means comprise hardware; and the mounting or towing means comprise a vehicle and associated hardware.

46. The apparatus of claim 40, wherein:

the signal-modifying means comprise means for substituting a signal representative of at least one period before or after the passing of the detritus, or both, in place of signal generated in response to the detritus.

* * * * *